US006184207B1

(12) United States Patent
Luke et al.

(10) Patent No.: US 6,184,207 B1
(45) Date of Patent: Feb. 6, 2001

(54) INHIBITORS OF PEPTIDE BINDING TO MHC CLASS II PROTEINS

(75) Inventors: Richard William Arthur Luke; Ronald Cotton, both of Macclesfield (GB)

(73) Assignee: Zeneca Limited (GB)

( * ) Notice: Under 35 U.S.C. 154(b), the term of this patent shall be extended for 0 days.

(21) Appl. No.: 09/319,870

(22) PCT Filed: Dec. 9, 1997

(86) PCT No.: PCT/GB97/03397

§ 371 Date: Jun. 14, 1999

§ 102(e) Date: Jun. 14, 1999

(87) PCT Pub. No.: WO98/25951

PCT Pub. Date: Jun. 18, 1998

(30) Foreign Application Priority Data

Dec. 12, 1996  (GB) .................................................. 9625865

(51) Int. Cl.$^7$ .............................. A61K 38/08; C07K 7/02; C07K 7/06
(52) U.S. Cl. .............................. 514/15; 514/16; 530/328; 530/332
(58) Field of Search .................................. 514/14, 15, 16; 530/327, 328, 332, 333, 334, 335, 338

(56) References Cited

U.S. PATENT DOCUMENTS 4,301,151 * 11/1981 Veber et al. ........................... 514/19

FOREIGN PATENT DOCUMENTS

93/05011 * 3/1993 (WO) .
96/30035 * 10/1996 (WO) .
97/16425 * 5/1997 (WO) .
97/31023 * 8/1997 (WO) .

OTHER PUBLICATIONS

Alexander et al. Development of High Potency Universal DR–Restricted . . . Immunity. vol. 1, pp. 751–761, Dec. 1994.*
Hoelzemann et al. Analysis of β–Turn Mimetics. Chemical Abstracts 120:218488h, Apr. 25, 1994.*

* cited by examiner

Primary Examiner—Jeffrey E. Russel
(74) Attorney, Agent, or Firm—Rothwell, Figg, Ernst & Manbeck

(57) ABSTRACT

The invention concerns pharmacologically useful peptide derivatives of the formula (I): P-AA$^1$-AA$^2$-AA$^3$-AA$^4$-AA$^5$-AA$^6$-AA$^7$-AA$^8$-Q, and pharmaceutically acceptable salts thereof, wherein either AA$^3$ together with AA$^4$, or AA$^4$ together with AA$^5$, or AA$^6$ together with AA$^7$ form a group of formula (II):

in which Ra is selected from hydrogen and (1–4C)alkyl, and the remainder of AA$^1$, AA$^2$, AA$^3$, AA$^4$, AA$^5$, AA$^6$, AA$^7$, and AA$^8$ are L-amino acid residues; P is a hydrophobic residue; and Q is OH, NH$_2$ or NRcRd. The invention further concerns processes for the manufacture of the novel peptide derivatives and the use of the compounds, and pharmaceutical compositions containing them, in treating MHC class II dependent T-cell mediated autoimmllne or inflammatory diseases, such as rheumatoid arthritis.

12 Claims, No Drawings

INHIBITORS OF PEPTIDE BINDING TO MHC CLASS II PROTEINS

The present invention relates to certain novel peptides which possess pharmacologically useful properties for use in treating autoimmune diseases or medical conditions, such as rheumatoid arthritis and other MHC class II dependent T-cell mediated diseases. The invention also includes pharmaceutical compositions of the novel peptides, processes for their manufacture, and their use in treating one or more of the aforementioned diseases or medical conditions and in the production of novel pharmaceuticals for use in such medical treatments.

Stimulation of the human immune response is dependent on the recognition of protein antigens by T cells. However T cells cannot respond to antigen alone and are only triggered by antigen when it is complexed with major histocompatibility complex (MHC) molecules on the surface of an antigen presenting cell, such as a B cell, macrophage or dendritic cell.

MHC class I molecules elicit a T-killer cell response which results in the destruction of the cell bearing the antigen. MHC class II molecules elicit a T-helper cell response which controls the expansion and maturation of selected B cells (i.e. antigen-specific antibodies) and activation of macrophages.

A critical requirement of the immune system is the ability to differentiate between "self" and "non-self" (i.e. foreign) antigens. This discrimination is required to enable the immune system to mount a response to invading foreign pathogens whilst maintaining tolerance to self-proteins and thereby preventing damage to normal tissues. An autoimmune disease results when self-tolerance breaks down allowing the immune system to react against self-tissues such as the joints in rheumatoid arthritis. It is thought that the maintenance of tolerance and thus avoidance of autoimmune disease is critically dependent on the function of MHC molecules.

The observation that many autoimmune diseases are linked to the inheritance of particular MHC alleles suggests a key role for MHC molecules in the pathogenesis of autoimmune disease. For instance multiple sclerosis is linked to the inheritance of HLA-DR2, insulin dependent diabetes mellitus to HLA-DR3 and/or HLA-DR4 and Hashimoto's thyroiditis to HLA-DR5. In particular, an especially strong association exists between predisposition to development of the chronic inflammatory joint disease rheumatoid arthritis and the inheritance of HLA-DR4Dw4 and/or HLA-DR4w14 and/or HLA-DR1. It is thought that the autoimmune disease associated MHC molecules bind to certain self-antigens and present them to T cells thus stimulating an autoimmune response. Other peptides which can bind to the autoimmune associated MHC molecules and/or either prevent the binding or displace already bound self-antigens and/or which inhibit T cell activation (especially the activity of pathogenic T-cells (e.g. Th 1 cells)) and/or which increase the activity of protective T-cells (e.g. Th 2 cells) or peptides which interact with MHC molecules by an alternative mechanism of action so as to prevent or modify stimulation of an autoimmune response mediated via said MHC molecules, may specifically suppress an autoimmune response.

An agent of this kind would offer therapy for the autoimmune disease whilst avoiding general suppression of the immune system, thus limiting deleterious side-effects. This kind of profile would have significant advantages over current therapy for diseases such as rheumatoid arthritis. It is contemporary practice to treat rheumatoid arthritis initially with symptom relief agents such as NSAIDs, which do not have any beneficial effect on disease progression and are often associated with unwanted side-effects. Treatment of more severe disease relies on the use of the so-called second-line agents. Often these are general cytotoxic compounds which are of limited efficacy and can cause severe toxicity problems. A rationally based, disease modifying agent, without associated non-specific cytotoxicity, would therefore offer significant benefits in the treatment of rheumatoid arthritis.

Peptides are disclosed in International Patent Application, Publication No's WO 92/02543, WO 93/05011 and WO 95/07707 which bind to MHC molecules and inhibit T-cell activation.

Although a number of peptides have been discovered which inhibit HLA-DR restricted T cell activation by binding to HLA-DR molecules, there is a continuing need for alternative compounds which bind to such molecules and/or either prevent the binding of self antigens or displace already bound self-antigens and/or inhibit T cell activation and/or increase the activity of protective T-cells, or which interact with MHC molecules by an alternative mechanism of action, so as to prevent or modify stimulation of an autoimmune response that cause a disease or condition referred to above.

We have discovered that the peptides of the present invention (set out below) surprisingly possess such pharmacologically useful properties and this is a basis for the present invention.

According to one aspect of the invention there is provided a peptide of the formula I (set out hereinafter) wherein either $AA^3$ together with $AA^4$, or $AA^4$ together with $AA^5$, or $AA^6$ together with $AA^7$ form a group of the formula II (set out hereinafter) in which Ra is selected from hydrogen and (1–4C)alkyl, and the remainder of $AA^1$, $AA^2$, $AA^3$, $AA^4$, $AA^5$, $AA^6$, $AA^7$ and $AA^8$ are L-amino acid residues;

P is a hydrophobic residue, and

Q is OH, $NH_2$ or NRcRd wherein Re is selected from (1–4C)alkyl, 2-carbamoylcyclopentyl, 2-pyridylmethyl, 4-carbamoylcyclohexyl, 4-carbamoylcyclohexylmethyl 3-carbamoylphenyl, 4-carbamoylphenyl, 4-(carbamoylmethyl)phenyl, 4-(carboxymethyl)phenyl, 2-morpholinoethyl and a group of the formula —$A^1$—$G^1$ in which $A^1$ is (3–7C) alkylene or $A^1$ is selected from
(1) a group of the formula -$A^2$-$B^2$- in which $A^2$ is p-phenylene or 1,4-cyclohexylene and $B^2$ is (1–4C)alkylene or $A^2$ is methylene and $B^2$ is p-phenylene or 1,4-cyclohexylene; and
(2) a group of the formula -$A^3$-$B^3$—$C^3$- in which $A^3$ is methylene, $B^3$ is p-phenylene or 1,4-cyclohexylene and $C^3$ is (1–3C)alkylene; and $G^1$ is a group of the formula —N=C[N(Rp)$_2$]$_2$ in which each Rp is independently selected from hydrogen, methyl, ethyl and propyl; and Rd is hydrogen or (1–4C)alkyl; or Q is 1-piperazinyl, 4-methyl-1-piperazinyl, 4-amidino-1-piperazinyl, 4-(2-(2-hydroxyethoxy)ethyl)-1-piperazinyl, 1-piperidyl or 4-substituted-1-piperidyl wherein the 4-substitutent is selected from carboxy, carbamoyl, N-(2-aminoethyl)carbamoyl and N-(4-aminobutyl)carbamoyl, or Q is a sequence of 1 to 6 amino acids or an amide thereof; or a pharmaceutically acceptable salt thereof.

It is to be understood that an amino acid of Q may independently have the D- or L-stereochemistry. Furthermore, when Q is defined as hydroxy (OH), this will be understood to be the hydroxy group of the C-terminal amino acid of $AA^8$. Similarly where Q is defined as $NH_2$, NRcRd, piperazinyl, piperidyl, etc., this means that the hydroxy group of the C-terminal amino acid $AA^8$ is replaced by such a group. It is also to be understood that where an amino acid is referred to this means an alpha-amino acid. It is also to be understood that when an L-amino acid is referred to this also includes amino acids such as Gly, 2,2-diethylGly. aza-alanine and aza-glycine which have no chiral carbon atom. It is further to be understood that generic terms such as "alkyl" include both straight and branched chain variants when the carbon numbers permit. The same convention applies to other radicals.

It is well known in the art that compounds having a chiral centre may exist in the form of a racemate (or a mixture of diastereoisomers where there is more than one chiral centre) or as an optically active enantiomer or diastereoisomer. It is also well known in the art that a particular biological activity associated with a racemic or diastereomeric mixture may result largely or solely from a single optically active isomer. It will therefore be understood that the invention concerns any form of a peptide of formula I which possesses the aforementioned pharmaceutically useful properties. It is well known in the art how to obtain a single optically active isomer, for example by separation from a racemic or diastereomeric mixture containing the isomer using conventional techniques, such as chromatography, or by chiral synthesis using an appropriate optically active starting material or intermediate, as exemplified herein. It is also well known in the art how to determine the pharmacological properties of such racemic or diastereomeric mixtures, and the individual optically active isomers, for example by using the assays described herein. The person skilled in the art is therefore easily able to obtain the particular isomers of the peptides of formula I having the beneficial pharmacological properties referred to herein.

It is also to be understood that the present invention also encompasses any polymorphic form, any tautomer or any solvate, or any mixture thereof, of a peptide of formula I which possesses the beneficial pharmaceutical properties referred to herein.

Suitable independent values for the a-amino acid residues $AA^1$, $AA^2$, $AA^3$, $AA^4$, $AA^5$, $AA^6$, $AA^7$ and $AA^8$, when they do not form part of a group of the formula II, include, for example, the 20 naturally occurring amino acids encoded by the genetic code, particularly alanine (Ala), glutamic acid (Glu), glycine (Gly), histidine (His), isoleucine (Ile), lysine (Lys), asparagine (Asn), glutamine (Gln), arginine (Arg), threonine (Thr), valine (Val) and proline (Pro). Amino acids such as sarcosine (Sar), 3,3,3-trifluoroalanine, 2,2-diethylglycine, 2,3-diaminopropanoic acid (Dap), 2,4-diaminobutanoic acid (Dab), 2-aminobutanoic acid (Abu), homoarginine, homophenylalanine, trans-4-hydroxyproline (Hyp), aza-alanine [$H_2N$—N($CH_3$)—COOH; Azala], aza-glycine [$H_2N$—NH—COOH; Azgly], 1,2,3,4-tetrahydroisoquinoline-3-carboxylic acid (Tic), octahydroindole-2-carboxylic acid (Oic), decahydroisoquinoline-3-carboxylic acid (Dic) are also suitable. (Where Dic is referred to this means the forms in which the ring-junctions both have the R configuration or both have the S configuration.) Corresponding $N^2$-methylated amino acids may also be used, as well as corresponding amino acids in which a free side-chain carboxylic acid function is esterified (for example as an (1–6C)alkyl or benzyl ester) and a free side-chain amino group is alkylated, (for example, methylated), acetylated or converted to a carbamate (for example, an alkyl (such as methyl or ethyl), phenyl or benzyl carbamate). Other suitable values include, for example, 2-substituted glycine in which the 2-substituent is a group of the formula —$(CH_2)_sNH_2$ wherein s is 1 to 3, or a group of the formula —$(CH_2)_pN(Re)_3^+.X^-$ wherein p is 2 to 4 and $X^-$ is a counter ion (such as acetate, trifluoroacetate, hydroxide or chloride), or a group of the formula —$(CH_2)_qN(Re)_2$ wherein q is 0 to 4 or a group of the formula —$(CH_2)_rN=C[N(Re)_2]_2$ wherein r is 1 to 4, wherein in which last three groups each Re is independently selected from hydrogen and (1–4C)alkyl (such as methyl or ethyl).

Particular values for Ra when it is alkyl include, for example, methyl, ethyl and propyl.

A preferred value for Ra includes, for example, hydrogen and methyl.

A suitable value for the hydrophobic residue P (which it will be appreciated is attached to the amino group of the N-terminal amino acid $AA^1$) includes, for example, an organic hydrophobic group such as a hydrophobic aliphatic, aromatic, heteroaromatic or mixed aliphatic/aromatic or aliphatic/heteroaromatic organic group of from 5 to 20 carbon atoms (and 1,2 or 3 heteroatoms selected from oxygen, sulphur and nitrogen for heteroaryl containing groups), for example a group of the formula R—, R.CO—, R.$SO_2$—, R.O.CO—, R.NHCO—, R.O.CS—, R.S.CO—, R.NHCS—, R.S.CS— and R.CS—, in which R includes, for example, (5–10C)alkyl, aryl, heteroaryl, aryl(2–10C)alkyl, heteroaryl(2–10C)alkyl, diaryl(2–8C)alkyl, aryl(2–10C)alkenyl, arylcyclopropyl, (5–10C)cycloalkyl, (5–10C)cycloalkyl(2–6C)alkyl, 3-biphenyl, 4-biphenyl, 4-cyclohexylphenyl, 2-naphthyloxymethyl, 3-naphthyloxymethyl, phenoxyphenyl and tetrahydronaphthyl, an aryl or heteroaryl group of which values of R may bear one or more (1–4C)alkyl, halogeno, cyano or (1–4C)alkoxy substituents. One particular embodiment of the invention includes, for example, compounds of the formula I in which P is R.CO— as defined above. A further particular embodiment of the invention includes, for example, peptides of the formula I wherein P is a hydrophobic aliphatic, aromatic or aliphatic/aromatic organic group of from 5 to 20 carbon atoms.

Particular values for R include, for example, when it is (5–10C)alkyl: pentyl, isopentyl, tert-pentyl, 2-methylpentyl, hexyl, isohexyl, 5-methylhexyl and octyl; when it is aryl: phenyl, naphthyl and indenyl; when it is heteroaryl: 2-, 3-, 5- or 6-indolyl, 2-, 3-, 5- or 6-indolinyl 2-, 3-, 5- or 6-benzo[b]thiophenyl, thienyl, 2-, 4- or 5-benzothiazolyl, 2-, 4- or 5-benzoxazoly, 2-, 4- or 5-benzimidazolyl, 1,4-benzodioxanyl attached at the 2-, 3-, 6- or 7-position and 2-, 3-, 5- or 6-benzofuranyl; when it is aryl(2–10C)alkyl: aryl (2–6C)alkyl (where the aryl portion includes, for example, any of the specific values for aryi given above and the (2–6C)alkyl portion includes, for example, methylene, ethylene, trimethylene, tetramethylene and pentamethylene) such as 2-phenylethyl, 3-phenylpropyl, 4-phenylbutyl and 5-phenylpentyl; when it is heteroaryl(2–10C)alkyl: heteroaryl(2–6C)alkyl (where the heteroaryl portion includes, for example, any of the specific values for heteroaryl given above and the (2–6C)alkyl portion includes, for example, methylene, ethylene, trimethylene, tetramethylene and pentamethylene) such as in 2-(2-cyanobenzo[b] thiophen-5-yl)ethyl; when it is diaryl(2–8C)alkyl: diaryl (2–6C)alkyl such as 2,2-diphenylethyl, 3,3-diphenylpropyl and 4,4-diphenylbutyl: when it is aryl(2–10C)alkenyl: aryl (2–6C)alkenyl such as styryl, 3-phenylpropen-2-yl and 4-phenylbuten-1-yl; when it is arylcyclopropyl: phenylcyclopropyl, 1-naphtlhylcyclopropyl and 2-naphthylcyclopropyl; when it is (5–10C)cycloalkyl: cyclopentyl, cyclohexyl and 1-adamantyl; and when it is (5–10C)cycloalkyl(2–6C)alkyl: 2-(cyclohexyl)ethyl, 3-(cyclohexyl)propyl and 4-(cyclohexyl)butyl. A particular value for a substituent on an aryl group of R includes, for example, methyl, ethyl, chloro, bromo, iodo, methoxy, ethoxy and cyano.

The hydrophobic residue P also includes, for example, a hydrophobic L-amino acid, such as phenylalanine (Phe) and hydrogenated analogues thereof such as cyclohexylalanine (Cha), para-chloroPhe, 3-(2-thienyl)alanine, tyrosine (Tyr), Tyr(Omethyl), tryptophan (Trp), biphenylalanine, 3-(1-naphthyl)alanine, 3-(2-naphthyl)alanine and hydrogenated analogues thereof, 3-(1-adamantyl)aianine (Ada), Glu (OBenzyl), 3-(benzyloxy)Ala, 3-(benzylsulfanyl)Ala and 9-fluorenylGly, each of which may optionally bear on the N-terminus a hydrophobic aliphatic, aromatic, heteroaromatic or mixed aliphatic/aromatic or aliphatic/heteroaromatic organic group as defined and exemplified above. Alternatively, the hydrophobic amino acid may optionally bear, for example, a further sequence of 1 to 3 amino acids selected from any of the suitable independent values for $AA^1$ to $AA^8$ defined above. For example P includes the particular sequences Ala-Cha. Ala-Ala-Cha, Tyr-Ala-Ala-Cha (SEQ ID NO: 4), Tyr-Ala-Ala-Phe (SEQ ID NO:5), Ala-Phe-Phe-Phe (SEQ ID NO:6) and Ala-Ala-Ala-Phe (SEQ ID NO: 7). The first amino acid of such further sequence of 1 to 3 amino acids (as read from left to right) may be an L- or D-amino acid and may also optionally bear a hydrophobic aliphatic, aromatic, heteroaromatic or mixed aliphatic/aromatic or aliphatic/heteroaromatic organic group as defined or exemplified above.

Further particular values for P include, for example, 3-(benzyloxycarbonyl)propionyl-Phe, 3-(benzyloxycarbonyl)propionyl-Cha, 4-(benzyloxycarbonyl)butyryl-Phe, 4-(benzyloxycarbonyl) butyryl-Cha, (5-oxo-pyrrolidin-2-yl)carbonyl-Phe-Tyr, (5-oxo-pyrrolidin-2-yl)carbonyl-Glu(OBenzyl)-Tyr, acetyl-Glu(OBenzyl)-Tyr, diphenylmethyl.CONH.CH$_2$CH$_2$.CO-Cha, diphenylmethyl.CONH.CH$_2$CH$_2$.CO-Tyr, diphenylmethyl.CONH.CH$_2$CH$_2$CH$_2$.CO-Cha, diphenylmethyl.CONH.CH$_2$CH$_2$CH$_2$.CO-Tyr, diphenylmethyl.NHCO.CH$_2$CH$_2$CH$_2$.CO-Cha, diphenylmethyl.NHCO.CH$_2$CH$_2$CH$_2$.CO-Tyr, benzyl.NHCO.CH$_2$CH$_2$.CO-Cha, benzyl.NHCO.CH$_2$CH$_2$.CO-Tyr, N-acetyl-4-chloro-beta-hydroxyPhe, 4-phenoxyphenyl.NHCO—, benzyl.NHCO.CH$_2$CH$_2$.CO.(N-methylPhe), benzyl.NHCO.CH$_2$CH$_2$.CONH.CH(CHPh$_2$).CO, benzyl.NHCO.CH$_2$CH$_2$.CO-Tyr, 3,3 -diphenylpropionyl, trans-cinnamoyl, 5-phenylvaleryl and 3-(2-cyanobenzo[b] thiophen-5-yl)propionyl.

A value for P of particular interest includes, for example, Ph.(CH$_2$)$_4$.CO— (5-phenylvaleryl (Phv)), Ph.(CH$_2$)$_4$.CS—, trans-cinnamoyl and 3-(2-cyanobenzo[b]thiophen-5-yl) propionyl.

A preferred value for the hydrophobic residue P includes, for example, 3-(2-cyanobenzo[b]thiophen-5-yl)propionyl and 5-phenylvaleryl (Phv), especially the latter.

When Rc is a group of the formula -$A^1$-$G^1$, a particular value for $A^1$ when it is alkylene includes, ior example, methylene, ethylene, propylene and butylene; a particular value for $B^2$ when is is (1–4C)alkylene includes, for example, methylene, ethylene and propylene, and a particular value for $C^3$ when it is (1–3C)alkylene includes, for example, methylene, ethylene and propylene.

A particular value for -$A^1$-$G^1$ includes, for example, 3-guanidinopropyl and 4-(2-guanidinoethyl)phenyl.

A particular value for Q when it is a sequence of 1 to 6 amino acids includes, for example, a sequence of L-amino acids independently selected from any of the suitable independent values for $AA^1$ to $AA^8$ defined above (such as Ala-Thr-Gly-OH), or their D-analogues, or a sequence containing both D- and L-amino acids, or an amide therof, such as an amide derived from ammonia, an (1–4C)alkylamine (such as methylamine) or a di(1–4C)alkylamine (such as dimethylamine). A particular group of values for Q includes, for example, those values where $R^4$ is not a sequence of 1–6 amino acids.

A preferred value for Q includes, for example, 4-carbamoyl-1-piperidyl (the residue of piperidine-4-carboxamide (Pip-NH$_2$)), 4-carboxy-1-piperidyl (the residue of piperidine-4-carboxylic acid (Pip-OH)), 4-(carbamoylmethyl)anilino (the residue of 4-aminophenylacetamide (Papa-NH$_2$)), 4-(carboxymethyl) anilino (the residue of 4-aminophenylacetic acid (Papa-OH)) and 4-(2-guanidinoethyl)anilino (the residue of 2-(4-aminophenyl)ethylguanidine (Pape-NHC(=NH)NH$_2$), especially Papa-NH$_2$.

A particular group of values for Q includes, for example, Pip-NH$_2$, Papa-NH$_2$, Pape-NHC(=NH)NH$_2$ and NHRc in which Rc is 3-guanidinopropyl, 2-morpholinoethyl or 4-(2-(2-hydroxyethoxy)ethyl-1-piperazinyl.

Preferred values for $AA^1$ to $AA^8$ (when they do not form part of a group of the formula II) include, for example, $AA^1$ selected from Ala, Ile, Tyr, Val, Glu, Lys, Arg, Gly, Gap, GapMe$_4$ and 3,3,3-trifluoroalanine, particularly Ala, Ile, Arg, Gap, GapMe$_4$, especially Ala, Arg and Ile, and more especially Arg;

$AA^2$ selected from Ala, Lys, Glu, Sar, Val, Arg, Gly, Pro, Ile, Tic, 3,3,3-trifluoroalanine and $N^6$-diethylLys, particularly Ala, Arg, Ile, Lys and Tic, especially Ala, Arg, Ile and Tic and more especially Ala;

$AA^3$ selected from Ala, His, Gln, Val, Thr, Glu, Gly, Asp, Asn and $N^3$-diethylDap, particularly Ala, His, Asp and Asn, especially Ala and Asn and more especially Ala;

$AA^4$ selected from Ala, Lys, Asn, Arg, Thr, Glu, Sar, Gly, Pro, His and $N^6$-diethylLys, particularly Ala, Arg, Lys and His, especially Ala, Arg and His and more especially Ala;

$AA^5$ selected from Thr, Val, Ala, Gly, Dap, Dab, Pro, Hyp, Asn, Ser and $N^3$-diethylDap, particularly Thr, Val and Dap, and especially Thr and Val;

$AA^6$ selected from Gly, Leu, Lys, Ala, Pro, Glu, Sar, His and Dap (especially Ala);

$AA^7$ selected from Pro, Ala, Lys, Arg, Glu, Sar, Gly, Oic and Dic (especially Ala); and $AA^8$ selected from from Ala, Gly, Dap, azaalanine and azaglycine, particularly Ala, Gly and azaglycine and especially Ala; and P and Q have any of the values, including the particular and preferred values, defined above. Where "Gap" is referred to this means an amino acid residue of the formula NH.CH[CH$_2$NH.C(=NH) .NH$_2$].CO—, and where "Gap Me$_4$" is referred to this means an amino acid residue of the formula —NH.CH (CH$_2$N=C[N(CH$_3$)$_2$]$_2$).CO—.

Particular independent groups of peptides of the present invention include, for example, peptides of the formula I wherein:

(1) AA³ together with AA⁴ form a group of the formula II;

(2) AA⁴ together with AA⁵ form a group of the formula II; and (3) AA⁶ together with AA⁷ form a group of the formula II; and wherein the other radicals have any of values, including the particular and preferred values, defined herein.

A preferred aspect of the present invention comprises peptides of the formula I which contain an arginine residue, particularly compounds in which AA¹ is arginine.

Compounds of the invention which are of particular interest include, for example, the specific embodiments set out hereinafter in the accompanying Examples.

Pharmaceutically acceptable salts include, for example, for peptides that are sufficiently basic, for example those having a free amino group, salts with acids forming physiologically acceptable anions, such as salts with mineral acids, for example, hydrogen halides (such as hydrogen chloride and hydrogen bromide), sulphonic and phosphonic acids, and with organic acids such as acetic, oxalic, tartaric, mandelic, p-toluenesulphonic, methanesulphonic trifluoroacetic acids and the like, and for peptides that are sufficiently acidic, for example those having a free carboxylic acid group, salts with bases forming physiologically acceptable cations, such as salts with alkali metal (such as sodium and potassium), alkaline earth metal (such as magnesium and calcium), aluminium and ammonium salts, as well as salts with suitable organic bases such as ethanolamine, methylamine, diethylamine, isopropylamine, trimethylamine and the like.

As stated above, the peptides of formula I, or a pharmaceutically acceptable salt thereof, will have beneficial pharmacological effect in warm-blooded animals (including man) in a range of autoimmune diseases or medical conditions, to treat symptoms or as a disease modifying agent or as a prophylactic treatment. Such diseases may include, for example, rheumatoid arthritis, multiple sclerosis, (Goodpasture's syndrome, idiopathic thrombocytopenic purpura, juvenile rheumatoid arthritis, coeilac disease, systemic lupus erythematosus, ankylosing spondylitis, Sjogren syndrome, myasthenia gravis, Type 1 (insulin dependent) diabetes, Hashimoto's disease, Grave's disease, Addison's disease, scieroderma, polymyositis, dermatomyositis, pemphigus vulgaris, bullous pemphigoid, autoimmune haemolytic anaemia, pernicious anaemia, glomerulonephritis, graft rejections and such like, especially rheumatoid arthritis and multiple sclerosis.

The utility of the peptides of the formula I, or a pharmaceutically acceptable salt thereof, may be assessed using a variety of standard tests and clinical studies, including those described in International Patent Application, Publication Nos. WO92/02543, WO93/05011 and WO95/07707 (or modifications thereof) and those described below. The peptides of formula I show significant activity in one or more of such tests or studies. Test A: Purified HLA-DR peptide in vitro binding assay. (This assay may be used to demonstrate the binding of the peptides of formula I to disease-associated MHC class II molecules.) 30 µl of biotin-FHA 307–320 (FHA (307–320) peptide, derivatised with long-chain biotin at the N-terminus, Biotin-Ahx-Pro-Lys-Tyr-Val-Lys-Gln-Asn-Thr-Leu-Lys-Leu-Ala-Thr-Gly-OH) (SEQ ID NO: 8) at 800 nM in phosphate buffered saline solution (PBS) is incubated with 30 µL of purified HLA-DR4Dw4 at a concentration between 0.5 and 5 µg/ml in V-welled micro-titre plates (Nunc) for 48 hours with or without inhibitor peptides. At the end of the incubation period 100 µl of the incubate is transferred to Enzyme Linked ImmunoSorbant Assay (ELISA) plates (Nunc) previously coated with an anti-MHC antibody (L243-American Type Culture Collection (ATCC) HB55 as described in Lampson and Levy (1980) J. Immunol. 125, 293–299) at a concentration of 10 µg/ml for 1 hour at room temperature and blocked thereafter for 1 hour with 1% bovine serum albumin (BSA) in PBS and 0.05% Tween 20. After a further 1 hour period the unbound peptide is washed away and a 1/4,000 dilution of streptavidin peroxidase (Sigma) in PBS with 0.01% of a suitable detergent such as NP-40 (Sigma) added for 2 hours at room temperature. After further washing tetramethylbenzidene (TMB) substrate solution (1 TMB tablet (Sigma) in 10 mls of 0.1M citrate/acetate buffer, pH 6.0 with 36 µl urea hydrogen peroxide (UHPO) (Fluka)) is added to each of the plates. The reaction is stopped by adding 2M sulphuric acid (10 µl per well) and the absorbance read at 450 nm to quantify the amount of peptide bound. The inhibitory activity of peptides is obtained by plotting absorbance against concentration.

The purified HLA-DR4Dw4 may be obtained as follows:

(i) Expression of HLA-DR in the Baculovirus system

The expression of recombinant proteins in insect cells from baculovirus vectors is an established procedure to obtain high yields of recombinant protein [Luckow, VA & Summers, MD (1988) Biotechnology 6 47–551]. To enable the expression of the heterodimeric HLA-DR eg. HLA-DR4Dw4 from a single recombinant baculovirus vector (as opposed to having separate recombinant viruses for the a and b chains and then doing a co-infection), a double-recombinant baculovirus is constructed which carries both the α and β chains.

A cDNA encoding the sequence of the α polypeptide is cloned into the transfer vector pacYM1 [Matsuura, Y; Possce, RD; Overton, HA & Bishop, DHL (1987) J. Gen. Virol 68, 1233–1250] to place expression of the protein under the control of the polyhedrin promoter. The unit is inserted into the baculovirus genome by homologous recombination in Sf21 insect cells to create a single recombinant baculovirus for the α chain. The techniques for the culture and infection of insect cells, for the homologous recombination and detection/isolation of recombinant viruses are all fully described by Summers, MDD & Smith GE (1987) [A Manual of Methods for Baculovirus Vectors and Insect Cell Culture Procedures; Texas Agricultural Experiment Station, Bulletin No. 1555]. The molecular genetic techniques used to construct the recombinant vectors are likewise readily available in the literature and are most fully described by Sambrook, J; Fritsch, EF & Maniatis T, (1989) [Molecular Cloning. A Laboratory Manual. 2nd Edition. Cold Spring Harbor Laboratory Press].

To create the double-recombinant baculovirus, a cDNA encoding the β chain is cloned into the transfer vector pAcUW1 [Weyer, U; Knight, S & Possee, RD (1990) J. Gen. Virol., 71, 1525–1534] to place expression of the protein under the control of the P10 promoter. The unit is then inserted into the genome of the single recombinant baculovirus carrying the α chain. Double-recombinant viruses are detected by spotting insect cells, infected with randomly picked viruses from the transfection, onto membranes and reacting them with a monoclonal antibody e.g. L243 which specifically recognises the HLA-DR heterodimer. Binding of the antibody to Sf21 insect cells is detected using standard flow cytometry techniques, readily available in the literature. Stable, double-recombinant baculovirus expressing HLA-DR are plaque-purified.

(ii) Purification of HLA-DR from insect cells

The method used is a modification of that described by Gorga et al 1987. (Gorga et al 1987. J. Biol. Chem. 262, 16087–16094). HLA-DR expressing baculovirus/Sf21 cells (10 L which is approximately equal to $2 \times 10^{10}$ cells) are solubilised in 100 ml of 5 mM EDTA (sodium salt), 50 mM Tris-HCL pH 8.5, 2% NP40, 150 nM NaCl, 1 mM iodoacetamide, 1 mM PMSF by homogenisation with 10 strokes of a teflon glass homogeniser. The homogenate is spun at 100,000 g for 1 hour and the supernatant collected. The anti-HLA-DR monoclonal antibody LB3.1 (Gorga et al 1986, Cell. Immunol. 103, 160–172) covalently coupled at a ratio of 50 mg of L243 to 10 ml of Protein A-Sepharose fast flow (Pharmacia) and pre-incubated with 10 mM Tris-HCl, pH 8.0, 0.1% NP-40 is incubated overnight with the supernatant. The resin is then put into a column and washed with 10 mM Tris-HCl, pH 8.0, 0.1% NP-40 (20 column volumes) followed by 0.15 M NaCl, 50 nM $Na_2HPO_4$, pH 7.0 1% octylglucoside (20 column volumes). The HLA-DR is eluted with 50 mM diethylamine pH 11.0, 0.15 M NaCl, 1% octylglucoside. Column fractions are immediately neutralised with 1 M Tris-HCl pH 8.0 and concentrated by ultracentrifugation through a centricon-10 membrane. Protein content is determined by a BCA protein assay (Pierce) and purity by SDA-PAGE electrophoresis.

In general, the peptides of formula I as defined above which were tested in test A showed significant inhibition at a concentration of about 10 $\mu$M or much less.

A further preferred aspect of the present invention comprises a peptide derivative of the formula I, or a pharmaceutically acceptable salt thereof, which does not bind to HLA-DR3 but binds to HLA-DR1 and/or HLA-DR4Dw4 and/or HLA-DR4Dw14. HLA-DR3 is a common HLA-DR allele which is not associated with rheumatoid arthritis. Accordingly, in rheumatoid arthritis patients who carry HLA-DR3 as one of their alleles (which is approximately one third of the total rheumatoid arthritis patients), such a peptide derivative of the formula I will not interfere with the normal role of HLA-DR3 in the host-defense function. The use of such a peptide derivative is therefore particularly advantageous for treating rheumatoid arthritis patients as it will result in less immunosuppression than would occur with a non-selective DR binder.

As a variant to test A, the ability of a peptide of the invention to bind to one or more HLA-DR molecules may be assessed as follows:

(i) Purification of HLA-DR Types from Cell lines

The method used is a modification of that described by Gorga et al, 1987, J.Biol.Chem. 262, 16087–16094. Human HLA-DR antigens is purified from various cell lines by immunoaffinity chromatography. Briefly, $1 \times 10^9$–$5 \times 10^9$ pelleted cells of the appropriate cell line selected from Hom 2 (source of DR1), BBF (source of DR2), AVL-B (source of DR3), JAH (source of DR4Dw4), JHAF (source of DR4Dwl3) or PE117 (source of DR4Dwl4) are solubilised at approximately 4° C. in 50 ml of 5 mM EDTA (sodium salt), 50 mM Tris-HCL pH 7.4, 2% NP40, 150 mM NaCl, 1 mM iodoacetamicle, 1 mM PMSF, by homogenisation with 10 strokes of a teflon glass homogeniser. The homogenate is spun at 100,000 g for 1 hour and the supernatant collected. The anti-HLA-DR monoclonal antibody LB3.1 (Gorga et al, 1986, Cell.Immunol., 103, 160–173) covalently coupled to CNBr-Sepharose 4B (Pharmacia) is pre-equilibrated with 150 mM NaCl, 50 mM Tris-HCL, pH 7.4, 0.1% NP-40 and incubated overnight with the supernatant. The resin is then packed in a column and washed with 0.15 M NaCl, 50 mM Tris-HCL, pH 7.4, 1% octylglucoside (20 column volumes).

The HLA-DR is eluted with 50 mM diethylamine pH 11.0, 0.15 M NaCl, 1% octylglucoside. Column fractions are immediately neutralised with 0.5 M HEPES NaOH pH 7.4. Protein content is determined by a Biorad protein assay and purity by SDS-PAGE electrophoresis.

(ii) Peptide Selectivity Binding Assays 200 nM biotin-$FHA_{307-320}$ in phosphate buffered saline (PBS) is incubated with either purified HLA-DR1, DR2, DR4Dw4, DR4Dwl3 or DR4Dwl4, (2–20 $\mu$g/ml) in V-well microtitre plates (Nunc) with or without inhibitor peptides in assay buffer (PBS, 0.01% NP40 (Sigma.)) For DR3 inhibition, 400 nM Biotin-Ahx-(D)Ala-Ala-Ala-Che-Ile-Ala-Ala-Ala-Thr-Leu-Lys-Ala-Ala-(D)Ala-OH is incubated with purified DR3 (20 $\mu$g/ml.), and incubated as above. After 48 hours, the incubates are treated, and absorbance readings taken as described in Test A. The inhibitory activity of peptides, expressed as $IC_{50}$ values, are calculated using Microcal Origin software on a PC.

Test B: Inhibition of T cell activation in vitro. (This assay may be used to demonstrate the ability of the peptides of formula I to inhibit a T cell immune response mediated by or through an MHC class II molecule).

Inhibitor peptides were tested for the ability to block stimulation of the B52.24 murine T cell hybridoma line which responds to the $FHA_{307-320}$ peptide (H-Pro-Lys-Tyr-Val-Lys-Gln-Asn-Thr-Leu-Lys-Leu-Ala-Thr-Gly-OH) (SEQ ID NO: 9) presented by HLA-DR4Dw4 molecules. B52.24 was produced by the fusion of lymph node T cells taken from $FHA_{307-320}$ immunised HLA-DR4Dw4 transgenic mice (International Patent Application, Publication No W095/03331) with the BW5147 murine T cell lymphoma line (White et al (1989) J. Immunol. 143, 1822) as outlined in Woods et al (1994) J. Exp. Med. 180, 173–181 and following the general methods for the generation of T cell hybridomas given in Current Protocols in Immunology, Volume 2, 7.21.

Inhibitor peptides at concentrations between 100 and 0.1 $\mu$M (or lower) were mixed with the antigenic peptide $FHA_{307-320}$ in-citlher varying concentrations between 100 and 0.1 $\mu$M or at a fixed concentration of 10 $\mu$M by dilution in RPMI-1640 culture media (Gibco) in a 96-well mictrotitre plate (Nunc) in a final volume of 100 $\mu$l. HLA-DR4Dw4 expressing B cells such as the JAH EBV transformed lymphoblastoid cell line (European Culture Collection ECACC 85102909) or B cells taken from an HLA-DR4Dw4 homozygous individual and transformed with Epsten Barr virus according to the method described in Current Protocols in Immunology 7.22.1 were fixed using gluteraldehyde by suspension in 1% gluteraldehyde (Sigma) at $4 \times 10^6$ cells/ml for 30 seconds, after which an equal volume of 200 mM lysine (Sigma) was added for 3 minutes. The cells were recovered by centrifugation at 300 g, washed in RPMI-1640 and added to the microtitre plates containing antigen and inhibitor compounds at a concentration of $2 \times 10^5$ cells per well. The microtitre plates were incubated for 2 hours at 37° C. and 5% $CO_2$.

The microtitre plates were then washed in RPMI-1640 by centrifugation at 300 g and aspiration twice before the addition of the B52.24 T cell hybridoma line at a concentration of $10^5$ cells per well in culture medium (RPMI-1640, 10% foetal calf serum (Gibco) and 2 mM glutamine (Gibco)). The microtitre plates were then incubated for a further 2 days at 37° C. and 5% $CO_2$. The plates were then centrifuged at 300 g for 10 minutes and 150 $\mu$l of supernatant removed from all wells to be frozen at –20° C. prior to bioassay for IL-2 content.

The culture plates containing supernatents to be assayed were left at room temperature to thaw and 100 ml of supernatent was transferred to fresh 96 round bottomed well plates. 1:1 serial dilutions of IL-2 were carried out using culture media (RPMI-1640 (Gibco), 10% foetal calf serum (Advanced Protein Products), 100 μg/ml streptomycin and 100 U/ml penicillin (Gibco), 2 mM L-glutamine (Gibco) and 50 μM 2-mercaptoethanol (Sigma)), to produce a standard curve of 250 units/ml to 0.04 units/ml IL-2 final. An IL-2 dependent cell line such as CTLL-2 cells (Nature (1977) 268 154–156) or HT-2 cells (J. Immunol. Methods (1987) 94–104) were harvested and washed twice using culture media prior to resuspension at $5 \times 10^4$ cells/ml. 100 μl of IL-2 dependent cell suspension was added to each well of the standard curve and test samples. The culture plates were incubated for 72 hrs at 37° C. and 5% $CO_2$. After which, 20 μl (1 mCi) of 3H-Thymidine (Amersham International) was added to each well and the plates returned to the incubator for a further 16 hrs. The contents of each plate were harvested onto glass fibre filter mats and the radioactivity measured using a betaplate scintillation counter.

In general, the peptides of formula I as defined above which were tested in test B showed significant inhibition at a concentration of about 10 μM or much less.

Test C: Peptide stimulated DTH (delayed type hypersensitivity) in BALB/C mice. (The assay may be used to demonstrate in vivo activity of peptides of formula I in an animal model). Balb/c female mice (18–20 g), 5 per group, were immunised sub-cutaneously on the flank with 0.1 ml of an emulsion of ovalbumin (Sigma) (2 mg/ml in saline) mixed 1:1 (v/v) with complete Freunds adjuvant (Sigma). Seven days later footpad thickness was detemined using a dual caliper micrometer followed by a challenge in one hind footpad with a 30 μl sub-plantar injection of 1% heat-aggregated ovalbumin protein in saline. Twenty-four hours after antigen challenge, footpads were measured and the DTH response calculated as the percentage increase in footpad thickness in the injected footpad compared to contralateral control. Inhibitors were adminstered by 3-day osmotic mini-pumps (Alzet) implanted 24 hours prior to antigen challenge at doses ranging from 10 mg/kg/day to 0.1 μg/kg/day. The degree of inhibition was calculated by subtracting the value for swelling of inhibitor treated footpads from that of the vehicle dosed controls, dividing by the control value and multiplying by 100%.

In general, the peptides of formula I as defined above which were tested in Test C showed significant inhibition at a dose of about 1 mg/kg/day or much less, without any overt toxicological or other untoward pharmacological effect.

Test D: (This assay may be used to demonstrate in vivo activity of peptides of formula I in an animal model of arthritis).

Balb/c female mice (19–21 g, 5–10/group) are immunised on day 0 and boosted on day 7 with a sub-cutaneous injection of 0.1 ml of an emulsion containing equal volumes of 2 mg/ml methylated bovine serum albumin (met-BSA, Sigma) in saline and complete Freund's adjuvant (Sigma) supplemented with 2.5 mg/ml Mycobacterium tuberculosis (MTB, strains C, DT and PN, MAFF, Weybridge, Surrey) thus giving a final MTB concentration of 3.5 mg/ml. An additional 0.1 ml i.p injection of $10^9$ Bordetella nertussis organisms (Wellcome Pertussis vaccine) in saline is given at the same time. Fourteen days later, animals are challenged into one knee joint with a 10 μl intra-articular injection containing 100 ug of met-BSA in saline using a 30 G needle and hamilton syringe. The contralateral knee is injected with a similar volume of saline and serves as a control. The degree of inflammation/swelling associated with both knees is determined 13 days later by measuring using a dual-caliper micrometer. This is achieved by making an incision with blunt-ended scissors and forceps into the skin approximately 5 mm above and below the knee and continuing along the side of the knee to form a flap which is then carefully cut away to expose the underlying joint. Measurements are made across the widest part of the knee, in the horizontal plane, on the flexed limb held in a fixed position. Percentage increase in inflammation in the antigen-injected knee compared to control is calculated according to the formula: [antigen-injected knee thickness—saline-injected knee thickness/saline-injected knee thickness]×100. Inhibitors are administered using 14 day osmotic mini-pumps (Alzet) implanted 24 hrs before antigen challenge at does ranging from 10 mg/kg/day to 0.1 ug/kg/day. The percentage inhibition of inflammation/swelling is calculated from the thickness measurements by subtracting the value for swelling in the inhibitor-treated group from that of the vehicle dosed controls, dividing by the control value and multiplying by 100. Additional assessments of disease involve 1) the histological evaluation of inflammation, synovitis and cartilage/bone erosions carried out on fixed knee sections stained with haemotoxylin and eosin and 2) the determination of levels of acute phase reactants in serum, serum amyloid P and/or haptoglobin.

Peptides of formula I as defined above may show in Test D significant inhibition at a dose of about 10 mg/kg/day or much less.

By way of illustration of the pharmacological activity of particular peptides of the formula I, the compound of Example 1 showed significant binding to HLA-DR4Dw4 in Test A at a concentration of 0.1 micromolar or much less, and was active at <0.1 mg/kg/day in Test C.

A peptide of formula I may be prepared by any process well known in the art of peptide chemistry to be applicable to the synthesis of analogous peptides.

A peptide of formula I may be obtained, for example, by procedures analogous to those disclosed in "Solid Phase Peptide Synthesis: A practical approach" by Atherton and Sheppard (published by IRL press at Oxford University Press, 1989). "Solid Phase Peptide Synthesis" by Stewart and Young (published by the Pierce Chemical Company, Illinois. 1984), "Principles of Peptide Synthesis" (published by Springer-Verlag, Berlin, 1984), and a series of books "Amino Acids, Peptides and Proteins" (volumes 1–25; volume 25 published in 1994) (published by the Royal Society of Chemistry, Cambridge, UK).

Preferably, a peptide of formula I is prepared by solid phase sequential synthesis. Using this technique, the amino acid which is to become the C-terminus amino acid of the peptide is protected at the alpha-amino group, and, if necessary, in the side chain and coupled to a solid support, for example a resin, such as 2-chlorotritylchloride resin or Merrifield resin (chloromethylpolystyrenc-divinylbenzene) if a free carboxylic acid is required after cleavage, or Rink Amide resin (4-(2',4'-dimethoxyphenyl-Fmoc-aminomethyl)-phenoxy resin) or Rink Amide MBHA resin (N-(4-[2',4'-dimethoxyphenyl-Fmoc-aminomethyl)-phenoxyacetamido-norleucyl)-4-methyl benzhydrylamine resin (all available from Calbiochem-Novabiochem) if a carboxamide is required after cleavage, whereafter the protecting group on the alpha-amino group is removed. The amino acid which is to be attached to the C-terminus amino acid is protected at the alpha-amino group and, if necessary, in the side chain and coupled to the C-terminus amino acid which remains attached to the solid support. The stepwise process of deprotection of the alpha-amino group and coupling to the next amino acid is repeated to give a protected or unprotected polypeptide attached to the solid support. The group of formula II is incorporated into the sequence by using an appropriately protected (3-amino-2-oxopiperidin-1-yl)alkanoic acid, obtained, for example, as described in the Examples (or by analogy therewith), in place of a protected amino acid. The protected or unprotected polypeptide is released from the solid support by standard procedures, for example using a mixture of trifluoroacetic acid, triethylsilane and water. It will be appreciated that a side-chain protecting group may be cleaved under the conditions used to release the peptide from the solid support, or may be cleaved as a separate step prior or subsequent to release of the peptide from the solid support. It will also be appreciated that the procedure to build up the polypeptide may be modified by using a sequence of two or more suitable protected amino acids in a particular coupling step. The synthesis may use manual techniques or be carried out automatically, employing for example, an Applied Biosystems 431A or 430A peptide synthesiser or Advanced Chemtech ACT357 peptide synthesiser or similar automatic peptide synthesiser, or a combination of both techniques can be used.

During the assembly of the peptides, the amino acid functional groups not taking part in the reaction are protected by various functional groups. For example, the N-terminal and side chain amino groups may be protected by using 9-fluorenylmethoxycarbonyl (Fmoc), t-butoxycarbonyl (Boc), biphenylisopropoxycarbonyl (Bpoc), 2-[3.5-dimethoxyphenyl]propyl-2-oxycarbonyl (Ddz), adamantyloxycarbonyl (Adoc), allyloxycarbonyl (Aloc), 2,2,2-trichloroethoxycarbonyl (Troc), benzyloxycarbonyl and various substituted benzyloxycarbonyl groups. These protecting groups can be cleaved when required by the standard techniques (e.g. acid or base treatment, catalytic hydrogenolysis and Pd(0) treatment or zinc/acetic acid treatment).

Suitable protecting groups used for the protection of the side chain guanidino group in the peptides containing an arginine residue include a nitro, adamantyloxycarbonyl, 4-methoxy-2,3,6-trimethylbenzenesulphonyl (Mtr), 2,2,5,7,8-pentamethylchroman-6-sulphonyl (Pmc) and (especially) 2,2,4,6,7-pentamethyldihydrobenzofuran-5-sulphonyl (Pbf) group.

Suitable protecting groups used for the protection of a side chain hydroxy group include t-butyl, benzyl and trityl (Trt). Suitable protecting groups used for the side chain imidazole group in the peptides containing a histidine residue, include a trityl, benzyl, tosyl, dinitrophenyl, Adoc, Boc or Fmoc group.

Suitable protecting groups used for the protection of a side chain carboxyl group include various esters (e.g. methyl, ethyl, t-butyl, benzyl, nitrobenzyl, allyl and 9-fluorenylmethyl).

The protecting group cleavage reactions can be performed at temperatures in the range of 4° C. to 40° C. (preferably at or about ambient temperature) and over a period of time in the range of 10 minutes to 24 hours.

Suitable coupling methods used for the coupling of the individual amino acids include the commonly used azide, symmetrical anhydride, mixed anhydride and various active esters and carbodiimides. In the case of various carbodiimides (e.g. dicyclohexyl- or diisopropyl-carbodiimides), a number of additives (e.g. 1-hydroxybenzotriazole (HOBT) and N-hydroxysuccinimde) may also be added. In addition, the amino acid couplings can also be achieved by using a number of other reagents, e.g. 1H-benzotriazole-1-yl-oxy-tris-pyrrolidinophosphonium hexafluorophosphate (PyBOP), (2-(1H-benzotriazole-1-yl)-1,1,3,3-tetramethyluronium tetrafluoroborate (TBTU) and (2-(1H-benzotriazole-1-yl)-1,1,3,3-tetramethyluronium tetrafluoroborate (HBTU). The coupling reactions can be performed at temperatures in the range of −20° C. and 40° C. and over a period of time in the range of 10 minutes to 24 hours. A suitable medium for carrying out the coupling reactions includes, for example, N,N-dimethylformamide (DMF). A particularly suitable method includes the use of HBTU, HOBT and diisopropylethylamine in DMF.

These and other methods of peptide synthesis are exemplified in the International Patent Applications referred to herein.

A hydrophobic residue P which is a group of the formula R—, R.CO—, R.SO$_2$—, R.O.CO—, R.NHCO—, R.O.CS—, R.S.CO—, R.NHCS—, R.S.CS— and R.CS— (or such a group present as a substituent on a terminal amino group of P where P is a hydrophobic amino acid or a hydrophobic amino acid bearing further amino acids) may be incorporated, for example, as a final step by alkylation, acylation or other standard functional group modification of a terminal amino group (for example prior to or subsequent to release of the peptide from the support). When C-terminus modifications are required (to obtain a particular value for Q), they may be performed after the peptide is synthesised, using conventional functional group modification. Alternatively a particular value for Q may be obtained by appropriate choice of the initial starting resin and/or the protected entity first coupled to the resin (for example by using a suitably protected group of the formula H—Q). Typical examples of the preparation of peptides of formula I are provided in the examples hereinafter.

A typical procedure for measuring the stability of a peptide of the present invention is as follows, in which, to minimize microbial contamination and degradation, all equipment that is used to prepare peptide solutions is sterilized in an autoclave and all material transfers carried out in a Class II laminar flow cabinet. Approximately 20 ml of McIlvaine's citric acid-phosphate buffer solution at pH 3 or 7.6 containing 0.02% sodium azide is filtered into a 50 ml bottle using a sterile 0.22 μm filter unit and a 20 ml syringe. Approximately 1.2 mg of peptide is accurately weighed in a capped vial. Using a sterile pipette tip, sufficient buffer solution is added to the peptide in the vial to give a peptide concentration of 0.1 mg/ml. The vial is capped and shaken to dissolve the peptide. Using a sterile pipette tip, aliquots of approximately 1 ml of the peptide solution are transferred to 10 HPLC vials, which are then capped. 5 vials are stored at −18 and 37° C. The area of the peptide peak for the solution is determined by HPLC using appropriate standards initially and after storage at −18 and 37° C. for 1, 2, 3 and 4 weeks. using a fresh vial at each time point with duplicate sample injections. The percentage of peptide remaining after storage at 37° C. at each time point is determined from the ratio of the area of the peptide peak at each time point to the initial area. Preferred peptides of the present invention have greater than 90%, and preferably greater than 95%, of peptide remaining after storage at 37° C. at both pH 3 and 7.6.

The peptides of formula I will generally be administered for therapeutic or prophylactic purposes to warm-blooded animals (including man) requiring such treatment in the form of a pharmaceutical composition, as is well known in the pharmaceutical art.

According to a further feature of the invention there is provided a pharmaceutical composition which comprises a peptide of the formula I, or a pharmaceutically acceptable salt thereof, in association with a pharmaceutically acceptable diluent or carrier.

The composition may be in a form suitable for oral use, for example a tablet, capsule, aqueous or oily solution, suspension or emulsion; for nasal use, for example a snuff, nasal spray or nasal drops; for vaginal or rectal use, for example a suppository; for administration by inhalation, for example as a finely divided powder or a liquid aerosol; for sub-lingual or buccal use, for example a tablet or capsule; or for parenteral use (including intravenous, subcutaneous, intramuscular, intravascular or infusion), for example a sterile aqueous or oily solution or suspension. The composition may be in a form suitable for topical administration such as for example creams, ointments and gels. Skin patches are also contemplated. Formulation in general is described in Chapter 25.2 of Comprehensive Medicinal Chemistry, Volume 5. Editor Hansch et al, Pergamon Press 1990.

In general the above compositions may be prepared in a conventional manner using conventional excipients. However, in the case of a composition for oral administration, it may be convenient for the composition to include a coating to protect the polypeptide active ingredient from the actions of enzymes in the stomach.

A preferred composition of the invention is one suitable for oral adminstration in unit dosage form for example a tablet or capsule which contains from 2.5 to 500 mg, and preferably 10 to 100 mg, of polypeptide in each unit dose, or one suitable for parenteral administration which contains from 0.5 to 100 mg of polypeptide per ml, and preferably 1 to 10 mg of polypeptide per ml of solution.

A parenteral composition is preferably a solution in isotonic saline or isotonic dextrose buffered if necessary to a pH of 5 to 9. Alternatively, the parenteral composition may be one designed for slow release in which case the amount of polypeptide per unit dose is in general greater than that required when a conventional injectable formulation is used. A preferred slow release formulation is a continuous release formulation, for example a formulation of the type described in European Patent Specification No. 58481 or, for peptides of formula I containing at least one basic group, a formulation as described in International Patent Application, Publication No. WO93/24 150. Certain peptides of the present invention possess solubility characteristics which make them particularly suitable for the manufacture and processing of slow release parenteral formulations, particularly formulations containing biodegradeabie polyesters such as polylactides, and for providing slow release formulations with beneficial release profiles. Furthermore, peptides of the present invention containing one or more basic groups, particularly arginine, can also form peptide-polymer salts with acid-ended polyesters, such as polylactides, and such peptides and peptide-polymer salts constitute a further aspect of the present invention. Certain such salts possess solubility characteristics which make them particularly suitable for the manufacture and processing of slow release parenteral formulations, for example as described in WO93/24150, and for providing slow release formulations with beneficial release profiles and storage stability characteristics. A preferred slow release parenteral formulation contains from 1 to 100 mg (such as 5 to 50 mg) of polypeptide per unit dose. A preferred slow release parenteral formulation is also one designed for slow release over a period of at least 5 days.

Preferred peptides of the present invention include those which, when in the form of an extruded polymer depot formulation, show minimal loss due to degradation on extrusion or which show minimal degradation on release from such a depot formulation. Typical procedures for measuring the level of degradation of a peptide of the present invention are as follows:

Preparation of Extruded Polymer Depot Formulation of Peptide

About 20 mg of peptide is accurately weighed and sufficient polymer (50/50% molar poly(D,L-lactic acid/glycolic acid) copolymer of approximate weight average molecular weight 20 kD and approximate polydispersity of 1.7 as determined by size exclusion chromatography relative to polystyrene standards) added to produce an approximate 20% w/w mixture. This is dissolved in anhydride-free glacial acetic acid to produce an approximate 10% w/v solution. The solution is freeze dried and the resulting freeze dried product is stored under vacuum prior to use.

About 100 mg of freeze dried material is loaded into the barrel of a small laboratory extruder and the plunger pushed down to consolidate the sample. The extruder is heated to between 90 and 95° C. and held at this temperature for 10 minutes before the freeze dried material is extruded under pressure to give a cylindrical extrudate of approximately 1 mm in diameter.

Analysis of Peptide Content of Extruded Polymer Depot Formulation of Peptide

Two approximate 5 mm lengths of extruded polymer depot containing peptide are accurately weighed and each dissolved in 1 ml of anhydride-free glacial acetic acid in separate 25 ml volumetric flasks. After about 1.5 hours the volume of each is made up to 25 ml with distilled water, causing the polymer to precipitate. The solids are filtered off using a 0.5 $\mu$m Millex PTFE filter and the solutions, A, collected.

A series of standard solutions are prepared from a stock solution of peptide in distilled water at 0.5 mg/ml and a stock solution of polymer in anhydride-free glacial acetic acid at 2.5 mg/ml as follows with each solutions made up to 10 ml with distilled water:

| Concentration of peptide ($\mu$g/ml) | Volume of stock polymer solution ($\mu$l) | Volume of stock peptide solution ($\mu$l) |
|---|---|---|
| 50 | 1000 | 1000 |
| 40 | 1000 | 800 |
| 30 | 1000 | 600 |
| 20 | 1000 | 400 |
| 10 | 1000 | 200 |
| 5 | 1000 | 100 |
| 0 | 1000 | 0 |

Each standard is filtered through a 5 $\mu$m Millex PTFE filter and an aliquot of filtrate, together with aliquots of the solutions A, analysed by HPLC using duplicate sample injections. The peptide content of the extruded polymer depot formulation of peptide is calculated from the concentration of peptide in solutions A, which is determined by comparing the area of the peptide peak in solutions A with the area of the peptide peak from the standard solutions. Preferred peptides of the present invention show minimal loss due to degradation on extrusion and thus the peptide content of the extruded polymer depot formulation is close to the approximate theoretical value of 20% w/w.

Degradation of Peptide on in vitro Release from an Extruded Polymer Depot

A solution of McIlvaine's citric acid-phosphate buffer solution at pH 7.6 containing 0.02% sodium azide, is filtered through a 0.22 $\mu$ filter and stored at 4° C. Approximately 10 mg of extruded ploymer depot containing peptide is placed in two small vials and 2 ml of the buffer solution added. The vials are then capped and stored in a water bath at 37° C. for a month. At suitable time points over a month, three 0.6 ml aliquots of release medium are removed from each vial and either analysed by HPLC or stored frozen in an HPLC vial at −18° C. prior to analysis by HPLC. 1.8 ml of the buffer solution is added to each vial containing the depot to replace the release medium that has been removed at each time point.

The average amount of intact peptide in the release medium at each time point is determined by HPLC using duplicate sample injections by comparing the area of the peptide peak in the release media with the area of the peptide peak from standard buffer solutions of peptide at known concentrations. The approximate average amount of peptide degradation products in the release media at each time point is determined by HPLC by comparing the area of additional new peaks in the release media with the area of the peptide peak from standard buffer solutions of peptide at known concentrations and assuming the extinction coefficient has not changed. The average cumulative in vitro release profile of intact peptide and total peptide (intact peptide and peptide degradation products) is determined from the amounts of intact peptide and peptide degradation products in the release medium at each time point.

Preferred peptides of the present invention show minimal degradation on in vitro release and thus show total peptide degradation products of less than 10% and preferably less than 5% of total peptide after a month of in vitro release into McIlvaine's buffer solution at pH 7.6 at 37° C.

The composition of the invention will generally be administered to man such that, for example, a daily dose will be from 10 micrograms to 5000 mg, preferably 0.1 to 100 mg, for a 70 kg patient, given in divided doses as necessary. The precise amount of composition administered and the route and form of administration may depend on the size, age and sex of the person being treated and on the particular disease or medical condition being treated and its severity, according to principles well know in the medical art.

A peptide of formula I, or a pharmaceutically acceptable salt thereof, may also be advantageously administered for therapeutic or prophylactic purposes together with one or more other pharmacological agents known in the general art to be of value in treating or relieving the symptoms of (or to be a disease modifying agent of) one or more of the diseases or medical conditions referred to hereinabove, such as a NSAID (such as ibuprofen or piroxicam), an analgesic (such as paracetamol), a corticosteroid, a muscle relaxant, a lipoxygenase inhibitor, methotrexate, azathioprine, D-penicillamine, Cyclosporin A or a monoclonal antibody therapy (such as-anti-CD4 or anti-TNF). In diabetes the peptides may be co-administered with insulin or other therapies for diabetes or diabetes complications, (such as an aldose reductase inhibitor). It is to be understood that such combination therapy constitutes a further aspect of the invention.

According to a further aspect of the present invention there is provided a method for treating a MHC class II dependent T-cell mediated autoimmune or inflammatory disease, for example one or more of the diseases or medical conditions referred to herein, which comprises administering to a warm-blooded mammal (including man) in need of such treatment an effective amount of a peptide of formula I, or a pharmaceutically acceptable salt thereof. The invention also provides the use of a peptide of formula I, or a pharmaceutically acceptable salt thereof in the production of a novel medicament for use in the treatment of a MHC class II dependent T-cell mediated autoimmune or inflammatory disease.

In addition to their aforesaid use in therapeutic medicine in humans, the peptides of formula I are also useful in the veterinary treatment of similar conditions affecting commercially valuable warm-blooded animals, such as dogs, cats, horses and cattle. In general for such treatment, the peptide of the formula I will be administered in an analogous amount and manner to those described above for administration to humans. The peptides of formula I are also of value as pharmacological tools in the development and standardisation of test systems for the evaluation of the effects of MHC class II molecules in laboratory animals such as cats, dotgs, rabbits, monkeys, rats and mice, as part of the continuing search for new and improved therapeutic agents, or as diagnostic reagents.

The invention will now be illustrated by the following non-limiting Examples in which, unless otherwise stated:

(i) concentrations and evaporations were carried out by rotary evaporation in vacuo;

(ii) operations were carried out at room temperature, that is in the range 18–26° C.;

(iii) yields, when given, are intended for the assistance of the reader only and are not necessarily the maximum attainable by diligent process development;

(iv) the following abbreviations are used: Phv=5-phenylvaleryl; Boc=tert-butoxycarbonyl; DMF=N,N-dimethylformamide; HOBT=1-hydroxy-benzotriazole; DIPCDI=diisopropylcarbodiimide; Met=methionine; Fmoc=9-fluorenyimethyloxycarbonyl; Fmoc-Pip-OH=N-(9-fluorenylmethoxycarbonyl)piperidine-4-carboxylic acid; Fmoc-Papa-OH=4-[N-(9-fluorenylmcthoxycarbonyl)amino]phenylacetic acid; CbZ=benzyloxycarbonyl, THF=tetrahydrofuran; DMSO=dimethylsulfoxide: HBTU=2-(1H-benzotriazol-1yl)-1,1,3,3-tetramethyluroniumhexafluorophosphate; DIPEA=diisopropylethylamine; TFA=trifluoroacetic acid; Su is succinimide attached via the ring nitrogen atom; tBu=tert-butyl; HPLC=high pressure liquid chromatography; and RP-HPLC=reverse phase high pressure liquid chromatography;

(v) flash chromatography was performed on Merck Kieselgel 60 (Art No. 9385) obtained from E Merck, Darmstadt, Germany;

(vi) $^1$H NMR spectra were determined at 200 Mhz in CDCL$_3$ or d$_6$-dimethylsulphoxide (d$_6$-DMSO) using tetramethylsilane (TMS) as an internal standard, and are expressed as chemical shift (delta) values in parts per million relative to TMS using conventional abbreviations for designation of major peaks: s, singlet; m, multiplet; t, triplet; br, broad, d, doublet; and (vii) where Fmoc-Arg(Pbf)-OH was used, this was in a commercially available form of a solvate containing one molecule of isopropyl ether (per molecule of Fmoc-Arg(Pbf)-OH).

EXAMPLE 1

Preparation of Phv-Arg-Ala-Ala-Ala-Thr-II-Ala-Papa-NH$_2$ (SEQ ID NO: 1)

1.1 Preparation of 2-[3-(9-fluorenyimethoxycarbonylamino)-2-oxopiperidin-1-yl]acetic acid (Fmoc-II-OH)

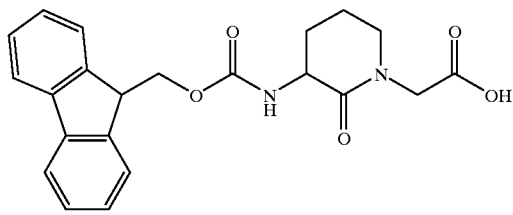

(a) (3RS)-3-aminopiperidin-2-one (1.5 g, obtained from DL-ornithine by the method described in Synthesis, 1978, 614–6) and triethylamine (1.4 ml) were dissolved in aqueous tert-butanol (50%, 30 ml) and heated to 40–50° C. Di-tert-butyl dicarbonate (2.4 g) was added in 4 portions over 2 minutes and the resulting solution was stirred at 50° C. for 20 minutes. Solvent was removed by evaporation and the residue was partitioned between ethyl acetate and water. The aqueous phase was extracted twice with ethyl acetate. The organic phases were combined, washed with brine, dried over Na$_2$SO$_4$ and solvent removed by evaporation. The resulting solid was recrystallised from cyclohexane to give (3RS)-3-tert-butoxycarbonylaminopiperidin-2-one as a white solid (1.6 g).

(b) (3RS)-3-tert-butoxycarbonylaminopiperidin-2-one (16.07 g) was dissolved in N,N-dimethylformamide (DMF, 350 ml) and the mixture was cooled to 0° C. Sodium hydride (3.6 g of a 50% dispersion in mineral oil) was added and then the mixture was stirred at 0° C. for one hour. A solution of ethyl bromoacetate (13.78 g) in DMF (20 ml) was then added. The mixture was stirred for 16 hours at ambient temperature, then cooled to 0° C. and ice added. Volatile material was removed by evaporation and the residue was partitioned between ethyl acetate and brine. The organic layer was washed with brine, dried over Na$_2$SO$_4$ and concentrated by evaporation. The resulting oil was purified on silica eluting with 40% ethyl acetate/petroleum ether (60–80° C.) to give ethyl 2-[(3RS)-3-tert-butoxycarbonylamino-2-oxopiperidin-1-yl]acetate as a colourless oil (18.15 g).

(c) Ethyl 2-[(3RS)-3-tert-butoxycarbonylarnino-2-oxopiperidin-1-yl]acetate (2.1 g) was refluxed in a mixture of acetone (30 ml), water (20 ml) and concentrated hydrochloric acid (12 ml) for 4 hours and the mixture was then evaporated to dryness. Water was added to the residue and the evaporation repeated. The residue was then dissolved in water (30 ml) and sodium bicarbonate (1.48 g) was added. 9-Fluorenyimethyl succinimidyl carbonate (2.48 g) was added in a mixture of acetonitrile (15 ml) and acetone (15 ml). Sodium carbonate (360 mg) was added to maintain the solution at approximately pH 8. The mixture was stirred for 16 hours and then volatile material was removed by evaporation. The residue was partitioned between water (10 ml) and ether (15 ml). The aqueous layer was separated and adjusted to about pH 2 with concentrated hydrochloric acid and extracted with ethyl acetate. The organic layer was washed with water (×10 ml), brine (15 ml), dried over Na$_2$SO$_4$ and evaporated to give 2-[(3RS)-3-(9-fluorenylmethoxycarbonylamino)-2-oxopiperidin-1-yl]acetic acid (Fmoc-II-OH) (1.01 g); NMR(CDCl$_3$): 1.65–2.05 (m, 4H), 3.25 (s, 2H), 3.9–4.1 (m, 3H), 4.14–4.35 (m, 3H), 7.25–7.45 (m, 4H), 7.5 (bd, 1H), 7.6 (d, 2H), 7.85 (d, 2H), 12.6 (bs, 1H); mass spectroscopy, m/e (positive fast atom bombardment (FAB+)) 395.11 (M+H)$^+$; microanalysis, found: C, 66.8; H, 5.70; N, 6.8%; C$_{22}$H$_{22}$N$_2$O$_5$; requires: C, 67.0; H, 5.62; N, 7.10%.

1.2 Synthesis of Phv-Arg-Ala-Ala-Ala-Thr-II-Ala-Papa-NH$_2$ (SEQ ID NO: 1)

The peptide was prepared by Fmoc solid phase synthesis starting with Fmoc Rink Amide MBHA Resin (Novabiochem, 0.50 g, 0.25 mmoles) in a Bond Elut tube (Varian, 15 ml, fitted with a filter in the bottom).

(a) The resin was deprotected using a 20% solution of piperidine in DMF (two treatments with 5 ml for 10 minutes each). After deprotection the resin was thoroughly washed with DMF (5×10 ml).

(b) Acylation was carried out by addition of a solution of Fmoc-Papa-OH (373 mg, 1 mmol), DMF(1.5 ml), HOBT (165 mg, 1 mmol) and diisopropylcarbodiimide (155 microlitres. 1 mmol). The coupling was left for approximately 30 minutes, washed with DMF (5×10 ml) and a small portion of the resin checked for completion of acylation using the Kaiser test (E. Kaiser, et al, (1970), Anal. Biochem. 34, 595).

The above deprotection (a) and coupling cycle (b) were repeated using,

| | |
|---|---|
| Fmoc-Ala-OH | (311 mg, 1 mmol); |
| Fmoc-II-OH | (198 mg, 0.5 mmol); |
| Fmoc-Thr(tBu)-OH | (397 mg, 1 mmol); |
| Fmoc-Ala-OH | (311 mg, 1 mmol); |
| Fmoc-Ala-OH | (311 mg, 1 mmol); |
| Fmoc-Ala-OH | (311 mg, 1 mmol); |
| Fmoc-Arg(Pbf)-OH | (752 mg, 1 mmol); |
| 5-Phenylvaleric Acid | (178 mg, 1 mmol); |

In each case the coupling time was around 30 minutes and a small portion of the resin was checked for completion of acylation by the Kaiser test. The phenylvaleric acid required a double couple to obtain a positive result by the Kaiser test.

The peptide was cleaved from the resin using a mixture of trifluoroacetic acid (7.9 ml) and triethylsilane (0.395 ml). After 2 hours the resin was washed with dichloromethane (approximately 150 ml) and the resulting solution evaporated to dryness. The resulting solid was partitioned between ether (25 ml) and water (25 ml) and then the ether was extracted with further portions of water (2×25 ml). The aqueous phases were combined and freeze dried.

The crude product was purified using preparative RP-HPLC (Vydac 218TP1022 column, 250 mm×22 mm), loading the crude material in 5 mls of 20% acetonitrile/water with 200 microiltres of DMF. Elution was with a gradient of acetonitrile-water containing 0.1%TFA (15–35% acetonitrile) over 80 minutes at a flow rate of 10 ml/minute. The fractions containing product were combined and freeze dried to give Phv-Arg-Ala-Ala-Ala-Thr-II-Ala-Papa-NH$_2$ (SEQ ID NO: 9) as a white solid (22 mg).

The product was characterised by HPLC, mass spectroscopy and amino acid analysis.

RP-HPLC (Vydac C18 column, 218TP54, 4.6×250 mm, eluting with acetonitrile and water containing 0.1% TFA, using a 10–50% acetonitrile gradient over 30 minutes, flow rate 1.0 ml/minute), retention time 18.88 minutes and 19.10 minutes (for the two diastereoisomers).

Mass spectrometry, m/e (positive electiospray (ES+)) 1006.7 (MH$^+$). Amino acid analysis (acid hydrolysis over 24 hours using a solution of 6N HCl containing 1% Phenol at 130° C.) gave Arg 1.04, Ala 4.12, Thr 0.85, II present.

EXAMPLE 2

Preparation of Phv-Arg-Ala-Ala-II-Ala-Ala-Ala-Papa-NH$_2$ (SEQ ID NO: 2)

The peptide was prepared by Fmoc solid phase synthesis starting from Fmoc Rink Amide MBHA Resin (Novabiochem, 0.50 g; 0.25 mmoles) by a mixture of automated synthesis and manual synthesis using a Bond Elut tube (Varian, 15 ml, fitted with a filter in the bottom).

Fmoc-Ala-Ala-Ala-Papa-NH-Resin was first obtained using an ACT 357 automated peptide synthesiser in multiple parallel synthesis mode by deprotecting the resin and sequentially coupling and deprotecting with Fmoc-Papa-OH (373 mg, 1 mmol), followed by three times with Fmoc-Ala-OH (311 mg, 1 mmol), following the manufacturer's recommended conditions for single acylations incorporating DIPCDI/HOBT chemistry. After deprotection, the resin was washed with DMF (10×10–20 ml). The carboxylic acid (1 mmol) was activated with DIPCDI (1 equivalent), HOBT (1 equivalent) in DMF for approximately 11 minutes before transfer to the resin. The acylation was carried out for approximately 60 minutes and then the resin was washed with DMF (10×10 ml). Fmoc deprotection at each stage was carried out using a 20% solution of piperidine in DMF (two treatments with 5 ml for 10 minutes each). After each deprotection, the resin was thoroughly washed with DMF (5×10 ml).

Fmoc-Ala-Ala-Ala-Papa-NH$_2$ resin was deprotected as described above and put in a Bond Elut tube. A solution of Fmoc-II-OH (198 mg; 0.5 mmol), DMF (1.5 ml), HBTU (379 mg; 1 mmol), HOBT(165 mg; 1 mmol) and DIPEA (348 microlitres; 2 mmol) was added to the resin. The coupling was left for approximately 30 minutes, washed with DMF (5×10 ml) and a small portion of the resin checked for completion of the coupling using the Kaiser test (E.Kaiser et al (1970), Anal. Biochem. 34, 595). The peptide resin was returned to the automatic synthesiser, deprotected as described above and the synthesis completed by sequentially coupling and deprotecting twice with Fmoc-Ala-OH (311 mg; 1 mmol), followed by Fmoc-Arg(Pbf)-OH (752 mg; 1 mmol) and 5-phenylvaleric acid (178 mg, 1 mmol) as previously described above for the automated couplings. The 5-phenylvaleric acid required a double couple to obtain a positive result by the Kaiser test. The peptide was then cleaved from the resin and purified by preparation RP-HPLC using similar methodology to that described for Example 1.2.

The product was characterised by HPLC, mass spectroscopy and amino acid analysis in a similar manner to that described for Example 1.2;

RP-HPLC (eluting with acetonitrile and water containing 0.1% TFA, using a 20–35% acetonitrile gradient over 15 minutes, flow rate 1.0 ml/minute), retention time 10.62 minutes. Mass spectrometry, m/e (ES+) 976.8 (M+H)$^+$, 500.0 (M+H+Na)$^{++}$. Amino acid analysis (acid hydrolysis over 24 hours using a solution of 6N HCl containing 1% Phenol at 130° C.) gave Ala 5.30, Arg 1.00, II present.

EXAMPLE 3

Preparation of Phv-Arg-Ala-II-Thr-Ala-Ala-Ala-Papa-NH$_2$ (SEQ ID NO: 3)

The peptide was prepared using similar methodology to that described for Example 2. by automated deprotection and coupling (using Fmoc-Rink Amide MBHA resin) of Fmoc-Papa-OH, Fmoc-Ala-OH (three times) and Fmoc-Thr(tBu)-OH and manual coupling of Fmoc-II-OH, followed by automated deprotection and coupling of Fmoc-Ala-OH, Fmoc-Arg(Pbf)-OH and 5-phenylvaleric acid. The peptide was cleaved from the resin, deprotected and purified by preparative RP-HPLC using a similar procedure to that described in Example 1.2. On this occasion the preparative RP-HPLC procedure separated the two diastereoisomers. The two diastereoisomers were characterised separately by HPLC, mass spectroscopy and amino acid analysis in a similar manner to that described for Example 1.2; RP-HPLC (eluting with acetonitrile and water containing 0.1% TFA, using a 20–35% acetonitrile gradient over 15 minutes, flow rate 1.0 ml/minute) retention time 11.34 minutes (Isomer A) and 11.62 minutes (Isomer B); mass spectroscopy (Isomer A), m/c (ES+): 1006.7 (M+H)$^+$, 514.8 (M+H+Na)$^{++}$; amino acid analysis (Isomer A; acid hydolysis over 24 hours using a solution of 6N HCl containing 1% phenol at 130° C.) gave Ala 4.32, Arg 1.00, Thr 0.757, II present.

EXAMPLE 4

The compounds of the invention may be administered for therapeutic or prophylactic use to warm-blooded animals such as man in the form of conventional pharmaceutical compositions, a typical example of which includes the following:

Injectable Solution 0.01 to 100 mg of active ingredient is dissolved in up to 2 ml of an aqueous injection vehicle to give a concentration of active ingredient between 0.01 to 100 mg/ml. The aqueous injection vehicle is buffered to a pH between 5 and 8 using a pharmaceutically acceptable buffer (for example, phosphate, or acetate) and contains a pharmaceutically acceptable tonicity adjustment agent (for example, sodium chloride or dextrose) added to achieve isotonicity. The vehicle may optionally also contain other pharmaceutically acceptable excipients such as solubilising agents (for example, DMSO, ethanol, propylene glycol or polyethylene glycol) preservatives and antioxidants. The active ingredient may typically be an Example described hereinbefore and may conveniently be present as a pharmaceutically acceptable salt.

CHEMICAL FORMULAE

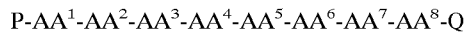

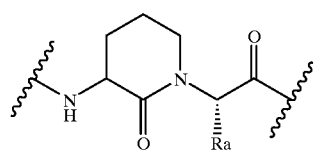

II

What we claim is:

1. A peptide of the formula I, P-$AA^1$-$AA^2$-$AA^3$-$AA^4$-$AA^5$-$AA^6$-$AA^7$-$AA^8$-Q, or a pharmaceutically acceptable salt thereof, wherein either $AA^3$ together with $AA^4$, or $AA^4$ together with $AA^5$, or $AA^6$ together with $AA^7$ form a group of the formula II

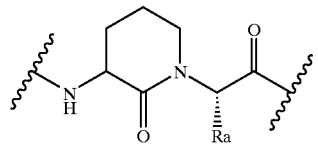

in which Ra is selected from hydrogen and (1–4C) alkyl, and the remainder of $AA^1$, $AA^2$, $AA^3$, $AA^4$, $AA^5$, $AA^6$, $AA^7$ and $AA^8$ are L-amino acid residues;

P is a hydrophobic residue; and

Q is $OH$, $NH_2$ or NRcRd wherein Rc is selected from (1–4C)alkyl, 2-carbamoylcyclopentyl, 2-pyridylmethyl, 4-carbamoylcyclohexyl, 4-carbamoylcyclohexylmethyl, 3-carbamnoylphenyl, 4-carbamoylphenyl, 4-(carbamoylmethyl)phenyl, 4-(carboxymethyl)phenyl, 2-morpholinoethyl and a group of the formnula -$A^1$-$G^1$ in which $A^1$ is (3–7C) alkylene or $A^1$ is selected from (1) a group of the formula -$A^2$-$B^2$- in which $A^2$ is p-phenylene or 1,4-cyclohexylene and $B^2$ is (1–4C) alkylene or $A^2$ is methylene and $B^2$ is p-phenylene or 1,4-cyclohexylene; and (2) a group of the formula -$A^3$-$B^3$—$C^3$— in which $A^3$ is methylene, $B^3$ is p-phenylene or 1,4-cyclohexyiene and $C^3$ is (1–3C)alkylene; and $G^1$ is a group of the formula —N═C[N(Rp)$_2$]$_2$ in which each Rp is independently selected from hydrogen, methyl, ethyl and propyl; and Rd is hydrogen or (1–4C)alkyl; or Q is 1-piperazinyl, 4-methyl-1-piperazinyl, 4-amidino-1-piperazinyl, 4-(2-(2-hlydroxyethoxy)ethyl)-1-piperazinyl, 1-piperidyl or 4-substituted-1-piperidyl wherein the 4-substituent is selected from carboxy, carbamoyl, N-(2-aminoethyl)carbamoyl and N-(4-aminobutyl)carbamoyl; or Q is a sequence of 1 to 6 amino acids or an amide thereof; or a pharmaceutically acceptable salt thereof.

2. A peptide, or a pharmaceutically acceptable salt thereof, as claimed in claim 1 in which P is a hydrophobic aliphatic, aromatic, heteroaromatic or mixed aliphatic/aromatic or aliphatic/aromatic or aliphatic/heteroaromatic organic group of 5 to 20 carbon atoms and 1, 2 or 3 heteroatoms selected from oxygen, sulphur and nitrogen.

3. A peptide, or a pharmaceutically acceptable salt thereof, as claimed in claim 1 or 2 wherein $AA^1$, $AA^2$, $AA^3$, $AA^4$, $AA^5$, $AA^6$, $AA^7$ and $AA^8$, when they do not form part of a group of the formula II, are selected as follows:

$AA^1$ is selected from Ala, Ile, Tyr, Val, Glu, Lys, Arg, Gly, Gap, $GapMe_4$ and 3,3,3-trifluoroalanine;

$AA^2$ is selected from Ala, Lys, Glu, Sar, Val, Arg, Gly, Pro, Ile, Tic, 3,3,3-trifluoroalanine and $N^6$-diethylLys;

$AA^3$ is selected from Ala, His, Gln, Val, Thr, Glu, Gly, Asp, Asn and $N^3$-diethylDap;

$AA^4$ is selected from Ala, Lys, Asn, Arg, Thr, Glu, Sar, Gly, Pro, His and $N^6$-diethylLys;

$AA^5$ is selected from Thr, Val, Ala, Gly, Dap, Dab, Pro, Hyp, Asn, Ser and $N^3$-diethylDap;

$AA^6$ is selected from Gly, Leu, lays, Ala, Pro, Glu, Sar, His and Dap;

$AA^7$ is selected from Pro, Ala, Lys, Arg, Glu, Sar, Gly, Oic and Dic; and $AA^8$ selected from from Ala, Gly, Dap, azaalanine and azaglycine.

4. A peptide, or a pharmaceutically acceptable salt thereof, as claimed in claim 1 or 2 in which $AA^4$ together with $AA^5$ form a group of the formula II.

5. A peptide, or a pharmaceutically acceptable salt thereof, as claimed in claim 1 or 2, in which $AA^6$ together with $AA^7$ form a group of the formula II.

6. A peptide, or a pharmaceutically acceptable salt thereof, as claimed in claim 1 or 2 wherein hydrophobic group P is 5-phenylvaleryl.

7. A peptide, or a pharmaceutically acceptable salt thereof, as claimed in claim 1 or 2 wherein Q is 4-carbamoyl-1-piperidyl, 4-carboxy-1-piperidyl, 4-(carbamoylmethyl) anilino, 4-(carboxymethyl)anilino or 4-(2-guanidinoethyl) anilino.

8. A peptide as claimed in claim 1, or a pharmaceutically acceptable salt thereof, which is selected from

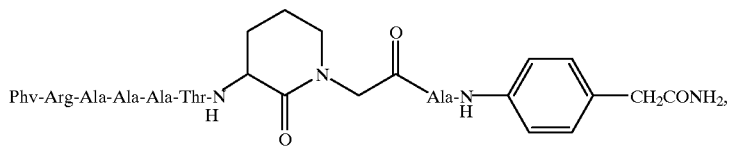

(SEQ ID NO:1)

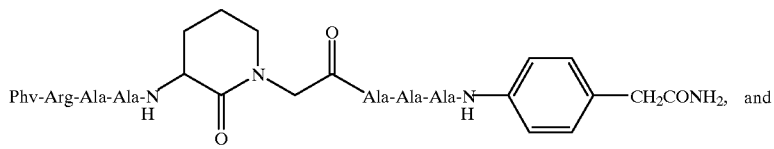

(SEQ ID NO:2) and

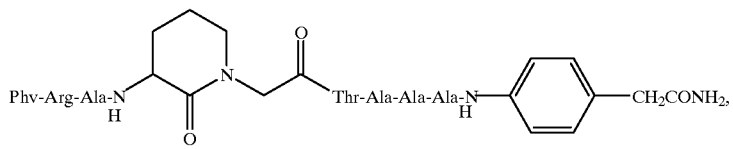

(SEQ ID NO:3)

or a pharmaceutically acceptable salt thereof, in which Phv represents a 5-phenylvaleryl group.

9. A pharmaceutical composition which comprises a peptide of the formula I, or a pharmaceutically acceptable salt thereof, as claimed in claim 1 or 2, in association with a pharmaceutically acceptable diluent or carrier.

10. A process for the manufacture of a peptide, or a pharmaceutically acceptable salt thereof, as claimed in claim 1, comprising sequentially coupling in an appropriate order suitably protected amino acids or sequences of two or more suitably protected amino acids, a suitably protected group of the formula H-II-OH and optionally a suitably protected group of the formula H-Q, followed by optional functional group modification of the N-terminal amino group to introduce a hydrophobic group P, and removal of any remaining protecting groups and any solid support.

11. A method for treating a MHC class II dependent T-cell mediated autoimmune or inflammatory disease which comprises administering to a warm-blooded mammal in need of such treatment an effective amount of a peptide of formula I, or a pharmaceutically acceptable salt thereof, as claimed in claim 1.

12. A method as claimed in claim 11 for treating rheumatoid arthritis or multiple sclerosis.

* * * * *

SEQUENCE LISTING

<160> NUMBER OF SEQ ID NOS: 9

<210> SEQ ID NO 1
<211> LENGTH: 6
<212> TYPE: PRT
<213> ORGANISM: Artificial Sequence
<220> FEATURE:
<221> NAME/KEY: MOD_RES
<222> LOCATION: (1)
<223> OTHER INFORMATION: 5-Phenylpentanoyl-Arg
<221> NAME/KEY: MOD_RES
<222> LOCATION: (6)
<223> OTHER INFORMATION: [(3-amino-2-oxopiperidin-1-yl)acetyl]-Ala-4-
      amino-phenyl-acetamide
<223> OTHER INFORMATION: Description of Artificial Sequence: Modified
      Sequence

<400> SEQUENCE: 1

Xaa Ala Ala Ala Thr Xaa
 1               5

<210> SEQ ID NO 2
<211> LENGTH: 6
<212> TYPE: PRT
<213> ORGANISM: Artificial Sequence
<220> FEATURE:
<221> NAME/KEY: MOD_RES
<222> LOCATION: (1)
<223> OTHER INFORMATION: 5-Phenylpentanoyl-Arg
<221> NAME/KEY: MOD_RES
<222> LOCATION: (4)
<223> OTHER INFORMATION: [(3-amino-2-oxopiperidin-1-yl)acetyl]-Ala
<221> NAME/KEY: MOD_RES
<222> LOCATION: (6)
<223> OTHER INFORMATION: Ala-4-aminophenylacetamide
<223> OTHER INFORMATION: Description of Artificial Sequence: Modified
      Sequence

<400> SEQUENCE: 2

Xaa Ala Ala Xaa Ala Xaa
 1               5

<210> SEQ ID NO 3
<211> LENGTH: 6
<212> TYPE: PRT
<213> ORGANISM: Artificial Sequence
<220> FEATURE:
<221> NAME/KEY: MOD_RES
<222> LOCATION: (1)
<223> OTHER INFORMATION: 5-Phenylpentanoyl-Arg
<221> NAME/KEY: MOD_RES
<222> LOCATION: (3)
<223> OTHER INFORMATION: [(3-amino-2-oxopiperidin-1-yl)acetyl]-Thr
<221> NAME/KEY: MOD_RES
<222> LOCATION: (6)
<223> OTHER INFORMATION: Ala-4-aminophenylacetamide
<223> OTHER INFORMATION: Description of Artificial Sequence: Modified
      Sequence

<400> SEQUENCE: 3

Xaa Ala Xaa Ala Ala Xaa
 1               5

<210> SEQ ID NO 4
<211> LENGTH: 4
<212> TYPE: PRT
<213> ORGANISM: Artificial Sequence
<220> FEATURE:
<221> NAME/KEY: MOD_RES
<222> LOCATION: (4)

```
<223> OTHER INFORMATION: cyclohexylalanine
<223> OTHER INFORMATION: Description of Artificial Sequence: Modified
      Sequence

<400> SEQUENCE: 4

Tyr Ala Ala Xaa
  1

<210> SEQ ID NO 5
<211> LENGTH: 4
<212> TYPE: PRT
<213> ORGANISM: Artificial Sequence
<220> FEATURE:
<223> OTHER INFORMATION: Description of Artificial Sequence: Modified
      Sequence

<400> SEQUENCE: 5

Tyr Ala Ala Phe
  1

<210> SEQ ID NO 6
<211> LENGTH: 4
<212> TYPE: PRT
<213> ORGANISM: Artificial Sequence
<220> FEATURE:
<223> OTHER INFORMATION: Description of Artificial Sequence: Modified
      Sequence

<400> SEQUENCE: 6

Ala Phe Phe Phe
  1

<210> SEQ ID NO 7
<211> LENGTH: 4
<212> TYPE: PRT
<213> ORGANISM: Artificial Sequence
<220> FEATURE:
<223> OTHER INFORMATION: Description of Artificial Sequence: Modified
      Sequence

<400> SEQUENCE: 7

Ala Ala Ala Phe
  1

<210> SEQ ID NO 8
<211> LENGTH: 14
<212> TYPE: PRT
<213> ORGANISM: Artificial Sequence
<220> FEATURE:
<221> NAME/KEY: MOD_RES
<222> LOCATION: (1)
<223> OTHER INFORMATION: Proline modified such that it has Biotin-Ahx
      covalently attached to it
<223> OTHER INFORMATION: Description of Artificial Sequence: Modified
      Sequence

<400> SEQUENCE: 8

Xaa Lys Tyr Val Lys Gln Asn Thr Leu Lys Leu Ala Thr Gly
  1               5                  10

<210> SEQ ID NO 9
<211> LENGTH: 14
<212> TYPE: PRT
<213> ORGANISM: Artificial Sequence
```

```
<220> FEATURE:
<223> OTHER INFORMATION: Description of Artificial Sequence: Modified
      Sequence

<400> SEQUENCE: 9

Pro Lys Tyr Val Lys Gln Asn Thr Leu Lys Leu Ala Thr Gly
1               5                   10
```